United States Patent [19]

Ebata et al.

[11] Patent Number: 4,987,256

[45] Date of Patent: Jan. 22, 1991

[54] PROCESS FOR PRODUCTION OF ALPHA-HYDROXYCARBOXYLIC ACID AMIDE

[75] Inventors: Shuji Ebata; Hiroyuki Hirayama; Takako Uchiyama, all of Niigata, Japan

[73] Assignee: Mitsubishi Gas Chemical Company, Inc., Tokyo, Japan

[21] Appl. No.: 550,150

[22] Filed: Jul. 9, 1990

[30] Foreign Application Priority Data

Sep. 7, 1989 [JP] Japan .................................. 1-230363

[51] Int. Cl.$^5$ ........................................... C07C 231/06
[52] U.S. Cl. .................................................... 564/126
[58] Field of Search ........................................ 564/126

[56] References Cited
U.S. PATENT DOCUMENTS 4,950,801  8/1990  Ebata et al. ...................... 564/126

Primary Examiner—Richard L. Raymond
Attorney, Agent, or Firm—Frishauf, Holtz, Goodman & Woodward

[57] ABSTRACT

Process for production of α-hydroxycarboxylic acid amide of the general formula (A), comprising hydrating cyanhydrin of the general formula (B) by the use of a modified manganese dioxide catalyst containing one or more of zirconium, vanadium, and tin, and an alkali metal element.

General Formula (I)

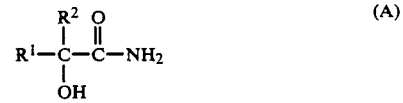

(A)

General Formula (II)

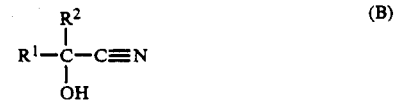

(B)

wherein all the symbols are as defined in the appended claims.

11 Claims, No Drawings

PROCESS FOR PRODUCTION OF ALPHA-HYDROXYCARBOXYLIC ACID AMIDE

BACKGROUND OF THE INVENTION

1. Field of the Invention

The present invention relates to a process for production of α-hydroxycarboxylic acid amide. More particularly, it relates to a process for producing α-hydroxycarboxylic acid amide by a hydration reaction of cyanhydrin in a liquid phase.

α-Hydroxycarboxylic acid amide is used as a starting material for production of α, β-unsaturated carboxylic acid ester through α-hydroxycarboxylic acid amide. In particular, in case of α-hydroxyisobutyric acid amide, methyl methacrylate is obtained through methyl α-hydroxyisobutyrate. This methyl methacrylate is very important for production of polymethyl methacrylate having excellent properties.

2. Description of Related Arts

Manganese dioxide as a catalyst for hydration of cyanhydrin into the corresponding α-hydroxycarboxylic acid amide is disclosed in West German Patent No. 2131813. δ-Type manganese dioxide as a catalyst for hydration of acetone cyanhydrin is described in U.S. Pat. No. 4,018,829.

In Japanese Patent Application Laid-Open Nos. 57534/1988 and 57535/1988, a process for preparation of a manganese dioxide catalyst in which zinc is introduced, and a process for preparation of a manganese dioxide catalyst by reducing potassium permanganate with hydrochloric acid are disclosed.

When, however, manganese dioxide prepared by the above processes is used as a catalyst as it is, problems arise in that catalytic activity is not sufficiently high, a large amount of the catalyst must be used, the yield of the desired amide is low, and the catalytic activity abruptly drops in a short time. Thus the processes have not been put into practical use.

It has been found that in production of α-hydroxycarboxylic acid amide from cyanhydrin, the activity of a manganese dioxide catalyst has a close relationship with zirconium, vanadium, or tin, and also with an alkali metal which exists in the catalyst. Based on the findings, the present invention has been accomplished.

SUMMARY OF THE INVENTION

The present invention relates to a process for production of α-hydroxycarboxylic acid amide represented by the general formula (A):

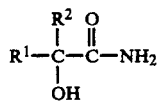

(A)

(wherein $R^1$ is a hydrogen, or an aliphatic hydrocarbon having 1 to 10 carbon atoms, and $R^2$ is an aliphatic, alicyclic or aromatic hydrocarbon group having 1 to 10 carbon atoms) from cyanhydrin represented by the general formula (B):

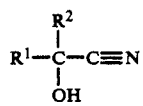

(B)

(wherein $R^1$ and $R^2$ are the same as defined above), which process comprises hydrating the cyanhydrin of the general formula (B) by the use of a modified manganese dioxide catalyst containing at least one element selected from zirconium, vanadium and tin, and containing an alkali metal element.

DESCRIPTION OF PREFERRED EMBODIMENTS

Cyanhydrin represented by the general formula (B) is easily obtained by reacting an oxo compound represented by the general formula (C):

(C)

(wherein $R^1$ and $R^2$ are the same as defined in the general formulas (A) and (B)) and hydrogen cyanide in the presence of a basic catalyst.

The modified manganese dioxide catalyst to be used in the present invention is prepared as described below.

As described above, manganese dioxide is used in a hydration reaction of cyanhydrin. Manganese dioxide generally refers to manganese oxide falling within the range of $MnO_{1.7}$ to $MnO_2$. In connection with a crystalline structure, α, β, γ, δ, ε-type, etc. are known. Furthermore, a transition between respective phases or a change in the crystallinity occurs so that its structure is very complicated and varied.

While manganese dioxide exists in nature, it is usually prepared by the oxidation of manganese (II) compounds or the reduction of manganese (VII) compounds on its use as a catalyst.

In preparation of the catalyst to be used in the present invention, it is preferred that both the manganese (II) compound and manganese (VII) compound are used because the type of crystal, the magnitude of specific surface area, and the type and amount of zirconium, vanadium, and tin, or alkali metal can be controlled.

The manganese dioxide catalyst to be used in the present invention is amorphous or nearly amorphous manganese dioxide having a large specific surface area, and a low crystallinity, in which one or more elements of zirconium, vanadium, and tin are introduced in an amount of 0.005 to 0.1 atom per atom of manganese, and an alkali metal element is introduced in an amount of 0.005 to 0.5 atom per atom of manganese.

As a method of uniformly adding zirconium, vanadium, tin, and alkali metal to manganese dioxide in preparation of the manganese dioxide catalyst to be used in the present invention, a coprecipitation method is preferably employed. This method can be carried out either in an acidic condition or in a basic condition. Preferably it is carried out in an acidic condition.

When the manganese dioxide catalyst is prepared in a basic condition, it is preferred that the resulting manganese dioxide catalyst is washed with, for example, diluted sulfuric acid before using in the present invention, in order to inhibit decomposition of cyanhydrin.

As a manganese (II) (divalent manganese) source to be used in preparation of the catalyst of the present invention, a water-soluble salt is chosen, and a sulfuric acid salt is particularly preferred. As a manganese (VII) (heptavalent manganese) source, water-soluble potassium permanganate, or sodium permanganate is particularly preferred. These compounds have an advantage that they can be also used as alkali metal sources.

As zirconium, vanadium, and tin sources to be used in preparation of the catalyst of the present invention, water-soluble salts are chosen, and sulfuric acid salts are particularly preferred.

The catalyst of the present invention can be prepared by the coprecipitation method. A water-soluble manganese (II) salt, and one or more compounds selected from water-soluble salts of zirconium, vanadium, or tin are dissolved in water, and mixed. The resulting solution is added to an aqueous solution of manganese (VII) compound, and mixed. The precipitate thus obtained is filtered, washed, and then dried.

The coprecipitation for preparation of the catalyst is carried out under atmospheric pressure or under pressure, and at an elevated temperature of 30 to 250° C., preferably 50 to 200° C. At lower temperatures than the above range, since the reaction of manganese (II) compound and manganese (VII) compound proceeds insufficiently, the yield of the modified manganese dioxide is low, and the alkali metal content therein is small. At higher temperatures than the above range, the surface area of the manganese dioxide is undesirably decreased.

In the hydration reaction of the present invention, the modified manganese dioxide catalyst as prepared above is used as a slurry catalyst in the form of powder, or is molded and used as a fixed bed catalyst.

The hydration reaction of the present invention is usually carried out in the presence of an excessive amount of water. The proportion of cyanhydrin in the feed material is 10 to 60% by weight, and preferably 20 to 50% by weight. If the oxo compound of the general formula (C) corresponding to the cyanhydrin of the general formula (B) is present in a proportion of 5 to 30% by weight in the feed material, decomposition of cyanhydrin is prevented and, as a result, there can be obtained an advantage that the yield of α-hydroxycarboxylic acid amide is increased.

In the process of the present invention, the reaction temperature is 20 to 100° C., and preferably 40 to 80° C. At lower temperatures than the above range, a rate of reaction is small. On the other hand, at higher temperatures than the above range, the amount of by-products due to decomposition of cyanhydrin is undesirably increased.

The hydration reaction of cyanhydrin according to the process of the present invention can be carried out either batchwise or continuously.

$R^1$ and $R^2$ in the general formulas (A) to (C) are defined as above. More specifically, $R^1$ and $R^2$ are independently a hydrogen, an aliphatic hydrocarbon having 1 to 10 carbon atoms (e.g. methyl group, ethyl group, propyl group, butyl group), an alicyclic hydrocarbon having 3 to 10 carbon atoms (e.g. cyclopentyl group, cyclohexyl group, cycloheptyl group) or an aromatic hydrocarbon having 6 to 10 carbon atoms (e.g. benzene, toluene, xylene).

In production of α-hydroxycarboxylic acid amide from cyanhydrin according to the process of the present invention, there is used a modified manganese dioxide catalyst in which the content of one or more metals selected from zirconium, vanadium, and tin is 0.005 to 0.1 atom per atom of manganese, and the content of alkali metal is 0.05 to 0.5 atom per atom of manganese. This modified manganese dioxide catalyst has high activity and a long service life. Thus the process of the present invention is of high significance from an industrial standpoint.

The present invention is described in greater detail with reference to the following examples.

COMPARATIVE EXAMPLE 1

(1) Preparation of Catalyst

A mixture of 178.5 g of an aqueous manganese sulfate solution (containing 14% by weight as Mn atom), 10.0 g of concentrated sulfuric acid, and 25 g of water was quickly added to a solution of 56.4 g of potassium permanganate dissolved in 560 g of water at a temperature of 70° C.

The precipitate thus obtained was aged at 90° C. for 3 hours, and then filtered off, washed four times with 1 liter of water, and then dried overnight at 110° C. to obtain 64.2 g of modified manganese dioxide.

In connection with the contents of metal components in the modified manganese dioxide, the ratio of potassium to manganese is 0.09/1 (atomic ratio).

(2) Reaction

The manganese dioxide obtained above was ground and sieved to 10–20 mesh. Then, 3.5 g of the 10–20 mesh manganese dioxide was packed in a jacketed glass tubular reactor with an inner diameter of 10 mm. Hot water maintained at 60° C. was passed in the jacket. A feed material prepared by mixing 20 g of acetone cyanhydrin, 60 g of water, and 20 g of acetone was passed through the tubular reactor at a flow rate of 5 g/hr.

The composition of the reaction solution after 5 hours as determined by high-performance liquid chromatography was as follows: 22.0% by weight of α-hydroxyisobutyric acid amide, 0.4% by weight of acetone cyanhydrin, 21.0% by weight of acetone, and 0.7% by weight of formamide. The yield of α-hydroxyisobutyric acid amide was 91% based on acetone cyanhydrin as the starting material.

The reaction was further continued. After 8 weeks, the composition of the reaction solution was analyzed. The yield of α-hydroxyisobutyric acid amide dropped to 75.3%.

EXAMPLE 1

(1) Preparation of Catalyst

A mixture of 138.7 g of an aqueous manganese sulfate solution (containing 14% by weight as Mn atom), 2.91 g of stannous sulfate, 23.9 g of concentrated sulfuric acid, and 20 g of water was quickly added at 70° C. to a solution of 66.4 g of potassium permanganate dissolved in 580 g of water.

The precipitate thus obtained was aged at 90° C. for 3 hours, and then filtered off, washed four times with 1 liter of water, and then dried overnight at 110° C. to obtain 68.2 g of modified manganese dioxide.

The contents of metal components in the modified manganese dioxide were: tin/potassium/manganese=0.02/0.09/1 (atomic ratio).

(2) Reaction

The same reaction as in Comparative Example 1 was carried out with the exception that 3.5 g of the manganese dioxide obtained in Example 1 (1) above was used.

The yields of α-hydroxyisobutyric acid amide after 5 hours and 8 weeks were 98% and 92%, respectively.

EXAMPLE 2

(1) Preparation of Catalyst

A mixture of 117.7 g of an aqueous manganese sulfate solution (containing 14% by weight as Mn atom), 11.6 g of stannous sulfate, 23.9 g of concentrated sulfuric acid, and 20 g of water was quickly added at 70° C. to a solution of 66.4 g of potassium permanganate dissolved in 580 g of water.

The precipitate thus obtained was aged at 90° C. for 3 hours, and then filtered off, washed four times with 1 liter of water, and then dried overnight at 110° C. to obtain 72.2 g of modified manganese dioxide.

The contents of metal components in the modified manganese dioxide were: tin/potassium/manganese=0.078/0.08/1 (atomic ratio).

(2) Reaction

The same reaction as in Comparative Example 1 was carried out with the exception that 3.5 g of the manganese dioxide obtained in Example 2 (1) above was used.

The yields of α-hydroxyisobutyric acid amide after 5 hours and 8 weeks were 96% and 91%, respectively.

EXAMPLE 3

(1) Preparation of Catalyst

A mixture of 138.7 g of an aqueous manganese sulfate solution (containing 14% by weight as Mn atom), 2.20 g of vanadyl sulfate, 23.9 g of concentrated sulfuric acid, and 20 g of water was quickly added at 70° C. to a solution of 66.4 g of potassium permanganate dissolved in 580 g of water.

The precipitate thus obtained was aged at 90° C. for 3 hours, and then filtered off, washed four times with 1 liter of water, and then dried overnight at 110° C. to obtain 67.5 g of modified manganese dioxide.

The contents of metal components in the modified manganese dioxide were: vanadium/potassium/manganese=0.02/ 0.09/1 (atomic ratio).

(2) Reaction

The same reaction as in Comparative Example 1 was carried out with the exception that 3.5 g of the manganese dioxide obtained in Example 3 (1) above was used.

The yields of α-hydroxyisobutyric acid amide after 5 hours and 8 weeks were 94% and 90%, respectively.

EXAMPLE 4

(1) Preparation of Catalyst

A mixture of 138.7 g of an aqueous manganese sulfate solution (containing 14% by weight as Mn atom), 4.80 g of zirconyl sulfate, 23.9 g of concentrated sulfuric acid, and 20 g of water was quickly added at 70° C. to a solution of 66.4 g of potassium permanganate dissolved in 580 g of water.

The precipitate thus obtained was aged at 90° C. for 3 hours, and then filtered off, washed four times with 1 liter of water, and then dried overnight at 110° C. to obtain 69.8 g of modified manganese dioxide.

The contents of metal components in the modified manganese dioxide were: zirconium/potassium/manganese=0.018/0.10/1 (atomic ratio).

(2) Reaction

The same reaction as in Comparative Example 1 was carried out with the exception that 3.5 g of the manganese dioxide obtained in Example 4 (1) above was used.

The yields of α-hydroxyisobutyric acid amide after 5 hours and 8 weeks were 97% and 95%, respectively.

EXAMPLE 5

(1) Preparation of Catalyst

A mixture of 138.7 g of an aqueous manganese sulfate solution (containing 14% by weight as Mn atom), 1.46 g of stannous sulfate, 2.40 g of zirconium sulfate, 23.9 g of concentrated sulfuric acid, and 20 g of water was quickly added at 70° C. to a solution of 66.4 g of potassium permanganate dissolved in 580 g of water.

The precipitate thus obtained was aged at 90° C. for 3 hours, and then filtered off, washed four times with 1 liter of water, and then dried overnight at 110° C. to obtain 68.9 g of modified manganese dioxide.

The contents of metal components in the modified manganese dioxide were: tin/zirconium/potassium/manganese=0.01/0.008/0.10/1 (atomic ratio).

(2) Reaction

The same reaction as in Comparative Example 1 was carried out with the exception that 3.5 g of the manganese dioxide obtained in Example 5 (1) above was used.

The yields of α-hydroxyisobutyric acid amide after 5 hours and 8 weedks were both 94%.

COMPARATIVE EXAMPLE 2

(1) Preparation of Catalyst

A mixture of 178.5 g of an aqueous manganese sulfate solution (containing 14% by weight as Mn atom), 10.0 g of concentrated sulfuric acid, and 25 g of water was quickly added at 70° C. to a solution of 50.7 g of sodium permanganate dissolved in 560 g of water.

The precipitate thus obtained was aged at 90° C. for 3 hours, and then filtered off, washed four times with 1 liter of water, and then dried overnight at 110° C. to obtain 63.3 g of modified manganese dioxide.

The contents of metal components in the modified manganese dioxide were: sodium/manganese=0.07/1 (atomic ratio).

(2) Reaction

The same reaction as in Comparative Example 1 was carried out with the exception that 3.5 g of the manganese dioxide obtained Comparative Example 2 (1) above was used.

The yields of α-hydroxyisobutyric acid amide after 5 hours and 8 weeks were 78% and 57%, respectively.

EXAMPLE 7

(1) Preparation of Catalyst

A mixture of 138.7 g of an aqueous manganese sulfate solution (containing 14% by weight as Mn atom), 2.91 g of stannous sulfate, 23.9 g of concentrated sulfuric acid, and 20 g of water was quickly added at 70° C. to a solution of 50.7 g of sodium permanganate dissolved in 580 g of water.

The precipitate thus obtained was aged at 90° C. for 3 hours, and then filtered off, washed four times with 1 liter of water, and then dried overnight at 110° C. to obtain 66.5 g of modified manganese dioxide.

The contents of metal components in the modified manganese dioxide were: tin/sodium/manganese=0.02/0.08/1 (atomic ratio).

(2) Reaction

The same reaction as in Comparative Example 1 was carried out with the exception that 3.5 g of the manganese dioxide obtained in Example 7 (1) above was used.

The yields of α-hydroxyisobutyric acid amide after 5 hours and 8 weeks were 81% and 75%, respectively.

EXAMPLE 8

(1) Preparation of Catalyst

A mixture of 138.7 g of an aqueous manganese sulfate solution (containing 14% by weight as Mn atom), 1.46 g of stannous sulfate, 2.40 g of zirconyl sulfate, 23.9 g of concentrated sulfuric acid, and 20 g of water was quickly added at 70° C. to a solution of 50.7 g of sodium permanganate dissolved in 580 g of water.

The precipitate thus obtained was aged at 90° C. for 3 hours, and then filtered off, washed four times with 1 liter of water, and then dried overnight at 110° C. to obtain 67.5 g of modified manganese dioxide.

The contents of metal components in the modified manganese dioxide were: tin/zirconium/sodium/manganese=0.009/0.01/0.08/1 (atomic ratio).

(2) Reaction

The same reaction as in Comparative Example 1 was carried out with the exception that 3.5 g of the manganese dioxide obtained in Example 8 (1) above was used.

The yields of α-hydroxyisobutyric acid amide after 5 hours and 8 weeks were 84% and 82%, respectively.

What is claimed is:

1. A process for producing α-hydroxycarboxylic acid amide represented by the general formula (A):

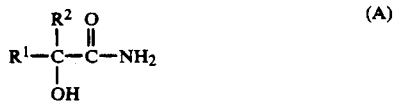

(wherein R$^1$ is a hydrogen, or an aliphatic hydrocarbon group having 1 to 10 carbon atoms, and R$^2$ is an aliphatic, alicyclic or aromatic hydrocarbon group having 1 to 10 carbon atoms) from cyanhydrin represented by the general formula (B):

(wherein R$^1$ and R$^2$ are the same as defined above), which process comprises hydrating the cyanhydrin of the general formula (B) by the use of a modified manganese dioxide catalyst containing at least one element selected from zirconium, vanadium, and tin, and containing an alkali metal.

2. The process as claimed in claim 1, wherein the cyanhydrin is acetone cyanhydrin.

3. The process as claimed in claim 1, wherein the alkali metal is sodium, potassium or a mixture thereof.

4. The process as claimed in claim 1, wherein the amount of at least one element selected from zirconium, vanadium and tin is 0.005 to 0.1 atom per atom of manganese.

5. The process as claimed in claim 1, wherein the amount of alkali metal is 0.05 to 0.5 atom per atom of manganese.

6. The process as claimed in claim 1, wherein the proportion of cyanhydrin in the feed material is 10 to 60% by weight.

7. The process as claimed in claim 1, wherein the hydration reaction is carried out at a temperature of 20 to 100° C.

8. The process as claimed in claim 1, wherein the hydration reaction is carried out batchwise or continuously.

9. The process as claimed in claim 1, wherein the modified manganese dioxide catalyst is prepared from a manganese (II) source and a manganese (VII) source by a coprecipitation method.

10. The process as claimed in claim 9, wherein the manganese (II) source is manganese sulfate.

11. The process as claimed in claim 9, wherein the manganese (VII) source is potassium permanganate or sodium permanganate.

* * * * *